United States Patent
Park et al.

(10) Patent No.: US 6,251,877 B1
(45) Date of Patent: *Jun. 26, 2001

(54) COMPOSITION FOR EXTERNAL APPLICATION CONTAINING A β-1,6-BRANCHED-β-1,3-GLUCAN

(75) Inventors: Kyung Mok Park, Yongin; Byung Hwa Park, Anyang; Sung So, Suwon; Mu Sung Kim, Suwon; Jung Su Kim, Suwon; Young Taek Kim, Youngin; Sung Gu Lee, Youngin; Dong Chul Lee, Seoul, all of (KR)

(73) Assignee: Pacific Corporation, Seoul (KR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/228,958

(22) Filed: Jan. 12, 1999

(30) Foreign Application Priority Data

Mar. 24, 1998 (KR) .................................................. 98-10098
Nov. 16, 1998 (KR) .................................................. 98-49026

(51) Int. Cl.⁷ .......................... A61K 31/715; A61K 7/00; A61K 31/716; C12P 19/04; C12N 1/14
(52) U.S. Cl. ............................ 514/54; 424/401; 435/101; 435/912
(58) Field of Search .................................... 435/101, 911; 424/401; 514/54

(56) References Cited

U.S. PATENT DOCUMENTS

| | | | |
|---|---|---|---|
| 3,898,959 | * | 8/1975 | Chen et al. ............... 195/28 R |
| 4,098,661 | * | 7/1978 | Kikumoto et al. .......... 204/160.1 |
| 4,833,131 | * | 5/1989 | Williams et al. ............ 514/54 |
| 4,954,440 | * | 9/1990 | Johal et al. .................. 435/101 |
| 5,320,849 | * | 6/1994 | Hagiwara et al. ............. 424/442 |
| 5,641,643 | * | 6/1997 | Tanaka et al. ................. 435/23 |

FOREIGN PATENT DOCUMENTS

| | | | |
|---|---|---|---|
| 5-286843 | * | 2/1993 | (JP) . |
| 67012000 | * | 8/1993 | (JP) . |
| 5-286843 | | 11/1993 | (KR) . |
| WO 9840082 | * | 9/1998 | (WO) . |

OTHER PUBLICATIONS

Eggensperger et al. "Multiactive polysaccharides. Part. 1. Fungi extracts", SOFW Journal. 1997, vol. 123, No. 8, pp. 542–546.*

Mansell et al. "Polysaccharides in Skin care". Cosmetics and Toiletries Magazine. Sep. 1994, vol. 109, pp. 67–72.*

Eggensperger et al., SOFW Journal . (1997), 123 (8), pp. 542–546.*

Gura et al., DECHEMA Biotechnology Conferences 5, 1992, pp. 569–572.*

Steiner et al. DECHEMA Biotechnology Conferences 1, 1988, pp. 149–154.*

Prokop et al. Experimental Mycology (1992), 16, pp. 197–206.*

* cited by examiner

Primary Examiner—Sandra E. Saucier
Assistant Examiner—Vera Afremova
(74) Attorney, Agent, or Firm—Foley & Lardner (57) ABSTRACT

Disclosed herein is a process for liquid cultivating *Schizophyllum commune* Fr. for isolation of β-1,6-branched-β-1,3-glucan and a composition for external application containing β-1,6-branched-β-1,3-glucan as an active ingredient, which can defer skin aging, impart skin whitening effect and cure skin damage effectively.

4 Claims, 3 Drawing Sheets

COMPOSITION FOR EXTERNAL APPLICATION CONTAINING A β-1,6-BRANCHED-β-1,3-GLUCAN

BACKGROUND OF THE INVENTION

1. Field of the Invention

The present invention relates to a process for liquid cultivating *Schizophyllum commune* Fr. for isolation of β-1,6-branched-β-1,3-glucan and a composition for external application containing β-1,6-branched-β-1,3-glucan obtained by the same.

2. Description of the Prior Art

The skin has a protection function against the surrounding environments such as change of temperature or humidity, ultraviolet, pollution materials. However, the normal function of the skin may be depressed by the excessive physical or chemical stimulation and stresses, or nutrient deficiency, causing skin-aging and skin-damage. So, in the cosmetic filed, for keeping the skin beautiful and healthy by preventing this hypergasia, physiological active materials derived from animals, plants or microorganisms have been used as a cosmetic ingredient.

For example, it has been reported that extracts of fungi have a moisture retention ability, inhibition ability of melanin-formation and screening ability of ultraviolet and thereby can be incorporated in a cosmetic composition to impart skin-whitening effect or anti-oxidative action. In particular, an extract of *Schizophyllum commune* Fr. to impact excellent skin whitening activity and moisture retention effect has been disclosed in JP-5-286843A.

However, its active component has not been revealed yet. That is to say, what component of the extract of *Schizophyllum commune* Fr. can impart effective skin action needs further research to be revealed. Such a further research may include improvement in method for effective and pure isolation of active components.

Therefore, the present inventors have conducted extensive studies in order to reveal active components of the extract of *Schizophyllum commune* Fr. to impact effective skin action. As a result, they found that β-1,6-branched-β-1,3-glucan obtained by liquid cultivation of *Schizophyllum commune* Fr. can inhibit melanin-formation, promote biosynthesis of skin-cells and collagen, and cure burn caused by excessive sun exposure.

Further, they found that yield of β-1,6-branched-β-1,3-glucan may be increased by adding an activated charcoal or glucose into the liquid medium. They also found that the yield of β-1,6-branched-β-1,3-glucan can be more increased by adding both activated charcoal and glucose into the liquid medium.

SUMMARY OF THE INVENTION

Thus, an object of the invention is to provide a process for liquid cultivating *Schizophyllum commune* Fr. for isolation of β-1,6-branched-β-1,3-glucan.

Further, other object of the invention is to provide a composition for external application containing β-1,6-branched-β-1,3-glucan obtained by the present process as an active ingredient, which can defer skin aging, impart skin whitening effect and cure skin damage effectively.

The object of the present invention can be accomplished by a process characterized in that it comprises steps of (1) preparing mycelia of *Schizophyllum commune* Fr.;

(2) cultivating the mycelia on a liquid medium with pH of 4.0~8.5 comprising 1~10% by weight of glucose, 0.1~1% by weight of yeast extract, 0.05~0.5% by weight of $(NH_4)_2HPO_4$ or $(NH_4)_2SO_4$, 0.05~0.5% by weight of $KH_2PO_4$ and 0.005~0.2% by weight of $MgSO_4 \cdot 7H_2O$;

(3) isolating β-1,6-branched-β-1,3-glucan from the liquid medium; and (4) purifying β-1,6-branched-β-1,3-glucan.

The present invention also provides a cultivation process further comprising a step of adding an activated charcoal into the liquid medium during the step(2).

The present invention also provides a cultivation process further comprising a step of adding a glucose into the liquid medium during the step(2).

The present invention also provides a cultivation process further comprising a step of adding both activated charcoal and glucose into the liquid medium during the step(2).

Further, the present invention provides a composition for external application characterized in that it contains β-1,6-branched-β-1,3-glucan obtained by the present process in an amount 0.00001~10% by weight, based on a total weight of the composition.

DETAILED DESCRIPTION OF THE INVENTION

*Schizophyllum commune* Fr. is woody rotting fungi belonging to Agaricales Tricholomataceae Schizophyllum of basidiomycetes in classification by Singer R. (The Agaricales in modern taxonomy, 1975) and excretes β-1,6-branched-β-1,3-glucan to the extracellular. It may be obtained in wild and identified by the following morphology or taxonomic characteristics: Its fruiting body has a size of 1.0~3.0 cm with no stipe and a shell-like shape with longitudinal gills and hair-densed edge The gill is white, but turns light grey or light purplish brown when it becomes ripe. Its flesh tends to shrivel, but to revive by absorbing moisture. The spore print is white. And, the spore has a cylindrical shape with a size of 4×1.5 μm~6×2 μm and is smooth and white. The *Schizophyllum commune* Fr. is scattered in a cluster on dead tree or stub of hardwood. Its regimen and shape are described in more detail in "Illustrated Book of Korean Fungus"(Sam soon KIM et al., YooPoong Press, 1990) and "The Agaricales in modern taxonomy"(Singer, R., 1975).

β type glucose bonds such as β-1,3-bond, β-1,4-bond, β-1,6-bond are generally named as β-glucan without specific distinction. But, actually, the bond type is very various depending on its origin, so as to have different physical or chemical properties and biological function. That is to say, β-glucan, depending on its origin, has different composition of constituent sugars, branch degree, molecular weight or 3-D structure. For example, the β-glucan of *Ganoderma licidum* is mainly isolated from the cell wall and minorly from the extracellular and has a bond of glucose, mannose and galactose. The β-glucan of *Coriolus versicolor* is mainly isolated from the cell wall and has β-1,3-bond and β-1,4-bond. The β-glucan of *Lentinus edodes* is isolated from the cell wall and is β-1,6-branched-β-1,3-glucan having two β-1,6-bonds branched to every five β-1,3-bonds of the main chain. The β-glucan of *Pleurotus ostreatus* is isolated from the cell wall and has a bond of glucose, mannose and galactose. The β-glucan of *Phelilinus linteus* is isolated from the cell wall and has a bond of 70~90% of glucose, and mannose and galactose. Further, the β-glucan of *Saccharomyces cerevisiae* is isolated from the cell wall and has an heterogeneous bond with little branch to be insoluble.

While, the β-glucan isolated from *Schizopyllum commune* Fr. according to the present invention was identified to be homogeneous β-1,6-branched-β-1,3-glucan having β-1,6-bond branched to every three β-1,3-bonds of the main chain, and composed only of glucose, with high molecular weight of 2,000,000~5,000,000. It is isolated from the extracellular and has stable and neutral polysaccharide properties.

The process for liquid cultivating from *Schizopyllum commune* Fr. for isolation of β-1,6-branched-β-1,3-glucan will be described in more detail.

(1) Step of Preparing Mycelia of *Schizophyllum commune* Fr.

The mycelia of *Schizophyllum commune* Fr. may be prepared by cultivating spores of wild type *Schizophyllum commune* Fr.

In detail, the spores of wild type *Schizophyllum commune* Fr., after several times washing with distilled water, are inoculated on yeast-malt extract agar medium{3 g of yeast extract, 3 g of malt extract, 5 g of peptone, 10 g of glucose, 15 g of agar, 1 l of distilled water} and maintained at a temperature of 24° C. for 7 days for induction of mycelia. The induced mycelia are cultivated slantingly in test tube containing the same yeast-malt extract agar medium, and then maintained at a temperature of 4° C. to be passage-cultured every 1 month.

(2) Step of Cultivating the Mycelia on a Liquid Medium

The mycelia are homogenized aseptically, and then are inoculated in an amount 0.00001~10% (v/v), preferably 3% (v/v) into liquid medium with pH of 4.0~8.5, preferably pH of 6.5, comprising 1~10% by weight of glucose, preferably 3% by weight; 0.1~1% by weight of yeast extract, preferably 0.3% by weight; 0.05~0.5% of $(NH_4)_2HPO_4$ or $(NH_4)_2SO_4$, preferably 0.05% by weight; 0.05~0.5% by weight of $KH_2PO_4$, preferably 0.1% by weight; and 0.005~0.2% by weight of $MgSO_4 \cdot 7H_2O$, preferably 0.05% by weight.

Then, the liquid cultivation of the mycelia is preformed by maintaining the medium at a temperature of 20~35° C., preferably 28° C. under an agitation of 100~400 rpm, preferably 200 rpm and an aeration of 0.3~2 vvm, preferably 1 vvm, in fermentation tank, for 3~7 days, preferably 5 days.

Figure 1:
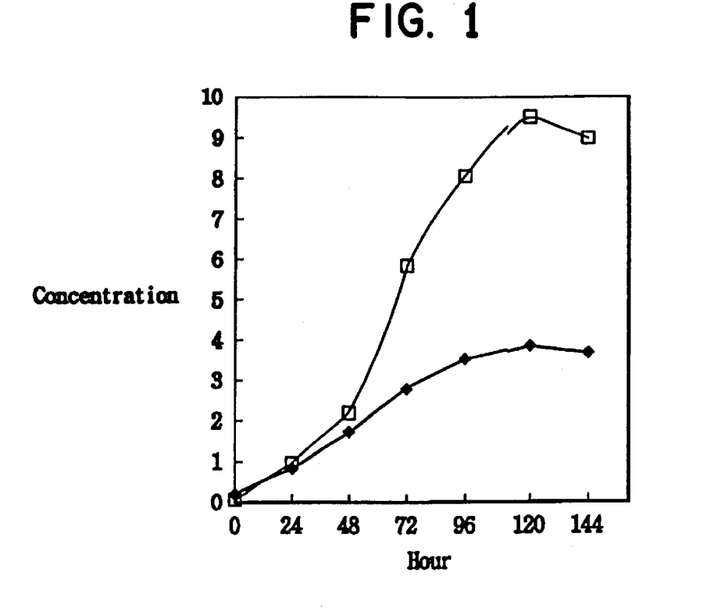
FIG. 1 is a graph showing growth of the mycelia of *Schizophyllum commune* Fr. (♦) and production amount of β-1,6-branched-β-1,3-glucan(□), depending on the cultivation time.

The graph shown in FIG. I teaches that the productivity of β-1,6-branched-β-1,3-glucan becomes to increase after the cultivation for 2 days and reaches to the maximum at the cultivation for 5 days. It may be understood that the cultivation for the first 2 days is for the growth of the mycelia and the cultivation thereafter is for the production of β-1,6-branched-β-1,3-glucan. And, in the later part of the cultivation β-1,6-branched-β-1,3-glucan may be somewhat decomposed. Therefore, the cultivation is preferable to be preformed for 5 days.

(3) Step of isolating β-1,6-branched-β-1,3-glucan from the Liquid Medium

β-1,6-branched-β-1,3-glucan can be isolated by means of adsorption with an activated charcoal powder.

In detail, after the cultivation is completed, the activated charcoal powder is added into the liquid medium in an amount of 0.1~6%, preferably 1%, and then the mixture is stirred to remove unnecessary components such as pigments and proteins. Then, the mixture is press-filtered to give a solution containing β-1,6-branched-β-1,3-glucan. At this time, the adsorption with the activated charcoal powder may be carried out after the press filtration.

(4) Step of Purifying β-1,6-branched-β-1,3-glucan

Purification of β-1,6-branched-β-1,3-glucan can be performed by means of precipitation with ethyl alcohol.

In detail, the obtained solution is fine- filtered with the filters having membranes with micropores of 1 μm and of 0.451 μm, in the order to give decolored or light brown filtrate. To the filtrate is added ethyl alcohol to precipitate β-1,6-branched-β1,3-glucan. For purification of β-1,6-branched-β-1,3-glucan, the precipitation with ethyl alcohol may be repeated 2~5 times. The amount of ethyl alcohol to be added is preferable in a range of 3~4 times, preferably 3.5 times as volume as that of the filtrate and can be reduced as the precipitation with ethyl alcohol are repeated.

In case that the precipitation with ethyl alcohol are repeated twice or more, the amount of ethyl alcohol to be added in final precipitation may be equivalent volume to that of the early filtrate.

Then, the precipitates are recovered, and hot-air dried at a temperature of 20~100° C. to remove volatile components such as ethyl alcohol. Finally, the product may be freeze dried at a temperature of −70° C, and then ground to give β-1,6-branched-β-1,3-glucan as powder.

In the cultivation step (2), as can be understood from FIG. 1, some materials to decompose β-1,6-branched-β-1,3-glucan and to inhibit the growth of the mycelia may be produced as side products, as well as β-1,6-branched-β-1, 3-glucan. These materials are identified as endo-1,3-β-glucanase and FIS(fruiting-inducing substance). Endo-1,3-beta-glucanase{Prokop et al. 1994. Can. J. Microbiol. Rev. vol. 40, no. 1, pp. 18} may decompose of β1,6branched-β-1,3-glucan to reduce the yield of β-1,6-branched-β-1,3-glucan And, the FIS, for example, (4E,8E)-N-D2'-hydroxypalirtoyl-1-O-β-D-glucopyranosyl-9-methyl-4,8-sphingadienine{Mizushina et al. 1998. Biochem. Biophys. Res. Commun. vol. 249, pp. 17} may inhibit the growth of the mycelia to reduce productivity of β-1,6-branched-β-1, 3-glucan{Wessels. 1978. Genetics and Morphogenesis in the Basidiomycetes. pp. 81~104. Academic Press; Prokop et al. 1992. Experimental Mycology. vol 16. pp. 197–206}. These side products have been reported to be produced in later part of the cultivation of *Schizophyllum commune* Fr.

Therefore, the present inventors, in order to remove these side products and thereby to increase the yield of β-1,6-branched-β-1,3-glucan, have conducted further studies. As a result, they found that the object can be accomplished by adding activated charcoal into the liquid medium during the cultivating step (2). That is to say, the side products can be removed by means of adsorption with activated charcoal, without any bad influence on the growth of the mycelia and the production of β-1,6-branched-β-1,3-glucan.

The addition of activated charcoal is preferable to be made after the cultivation for 2~4 days, in an amount of 0.1~5%. After the addition, the cultivation may The continued for further 1~4 days.

The addition of activated charcoal can increase the yield of β-1,6-branched-β-1,3-glucan by about 30%.

Besides, the yield of β-1,6-branched- β1,3-glucan can be further increased by supply of glucose during the cultivation for production of β-1,6-branched-β-1,3-glucan.

In detail, high C/N ratio may improve the productivity of β-1,6-branched-β-1,3-glucan, while low C/N ratio may promote the growth of the mycelia. Therefore, in the present invention, the liquid medium may be made to relatively low C/N ratio by reducing the initial amount of the carbon source, comparing 1~3% of glucose and 0.3~0.5% of yeast extract during the cultivation for the growth of the mycelia, while to relatively high C/N ratio, by supply of glucose during the cultivation for the production of β-1,6-branched-β-1,3-glucan. The supply of glucose is preferable to be made when the production of β-1,6-branched-β-1,3-glucan becomes to rapidly increase or the growth of the mycelia goes to slow, that is to say, after the cultivation for 3~5 days, in an amount of 1~10%. After the supply, the cultivation may be continued for further 1~3 days. The supply of glucose can increase the yield of β-1,6-branched-β-1,3-glucan by about 38%.

Further, the yield of β-1,6-branched-β-1,3-glucan can be furthermore increased by adding both activated charcoal and glucose into the liquid medium. The addition is preferable to be made after the cultivation for 3~5 days. The initial medium is preferable to comprise 1~3% of glucose and 0.3~0.5% of yeast extract as a carbon source, in order to lower the C/N ratio. The amount of activated charcoal and glucose to be added are preferably 0.1~5% and 1~10%, respectively.

After the addition, the cultivation may be continued for further 1~5 days. The addition can increase the yield of β-1,6-branched-β-1,3-glucan by about 60%.

Figure 4:
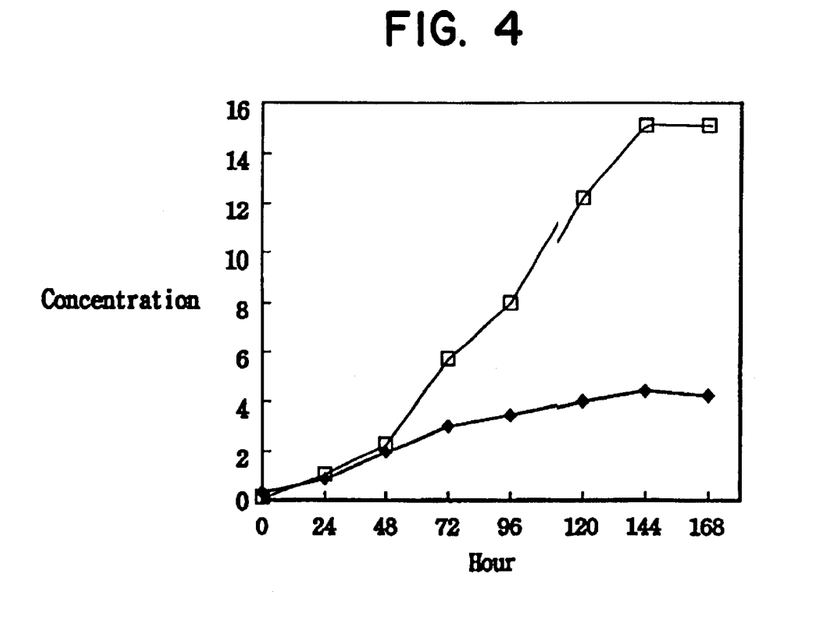
FIG. 4 is a graph showing growth of the mycelia of *Schizophyllum commune* Fr. (♦) and production amount of β-1,6-branched-β-1,3-glucan(□), depending on the cultivation time, in the process comprising 2nd cultivation step wherein both activated charcoal and glucose are added into the liquid medium.

The graph shown in FIG. 4 teaches that the productivity of β-1,6-branched-β-1,3-glucan becomes to increase after the cultivation for 2 days and reaches to the maximum at the cultivation for 6 days. It may be understood that the additions of activated charcoal and glucose can increase the productivity and lengthen the production term, resulting in increasing the yield of β-1,6-branched-β-1,3-glucan.

β-1,6-Branched-β-1,3-glucan obtained by the above process, as shown in the following experimental examples, can promote biosynthesis of skin-cells and collagen, cure burn caused by excessive sun exposure and inhibit melanin-formation.

Based on these results, the present invention can provide a composition for external application containing β-1,6-branched-β-1,3-glucan as an active ingredient. The composition can defer skin aging, impart skin whitening effect, and cure skin damage effectively. The composition may contain β-1,6-branched-β-1,3-glucan in an amount of 0.00001~10% by weight, which can be chosen depending on the formulations or the final purposes of the composition. Further, the composition for external application may be formulated, but not limited thereto, cosmetic such as skin softener, nutrient toilet water, massage creams, nutrient creams, pack and gel, and topicum such as lotion, ointment, gel, cream, patch or spray. Also, the compositions may further comprise other components, which have been conventionally used and can be chosen depending on the formulation.

PREFERRED EMBODIMENTS OF THE INVENTION

The present invention will be illustrated in more detail by way of the following Examples. However, these examples are provided for only illustration purpose and should not be constructed as limiting the scope of the invention which is properly delineated in the accompanying claims.

Preparation 1

The mycelia of *Schizophyllum commune* Fr. were cultured slantingly in test tube containing yeast-malt extract agar medium{3 g of yeast extract, 3 g of malt extract, 5 g of peptone, 10 g of glucose, 15 g of agar, 1 l of distilled water} and then homogenized aseptically.

Then, the mycelia were inoculated in an amount of 3% (V/V) into a liquid medium with pH of 6.5 comprising 3% by weight of glucose, 0.3% by weight of yeast extract, 0.05% of $(NH_4)_2HPO_4$, 0.1% by weight of $KH_2PO_4$ and 0.05% by weight of $MgSO_4 \cdot 7H_2O$. The liquid cultivation was performed by maintaining the medium at a temperature of 28° C., under an agitation of 200 rpm and an aeration of 1 vvm, in fermentation tank of 30 l, for 5 days. After the cultivation was completed, the concentration of the mycelia was about 4.0 g/l and the concentration of β-1,6-branched-β-1,3-glucan was about 9.5. g/l (See FIG. 1).

Next, to the liquid medium was added, activated charcoal powders(Jeil Chemical Co., Ltd., Korea) in an amount of 1.0%, and then the mixture was stirred for 30 minutes. Then, the mixture was press-filtered to give a solution containing β-1,6-branchedβ1,3-glucan.

Again, the solution was filtered with the filters having membrane micropores of 1 $\mu$m and of 0.45 $\mu$m, in this order to give decolored or light brown filtrate. To the filtrate was added 3.5 times volume of ethyl alcohol, and then the mixture was maintained at a room temperature overnight, to be precipitated. The precipitate was recovered and dissolved in distilled water, to give a solution having an equivalent volume to that of the early filtrate. To the solution was added 2 times volume of ethyl alcohol, and then the mixture was maintained at a room temperature overnight, to be precipitated. Again, the precipitate was recovered and dissolved in distilled water, to give a solution having an equivalent volume to that of the early filtrate. To the solution was added an equivalent volume of ethyl alcohol, and then the mixture was maintained at a room temperature overnight, to be precipitated. Then, the precipitate was recovered and heated air dried at 80° C. Finally, the product was freeze dried at −70° C, and then ground with grinder, to give the powder.

Figure 2:
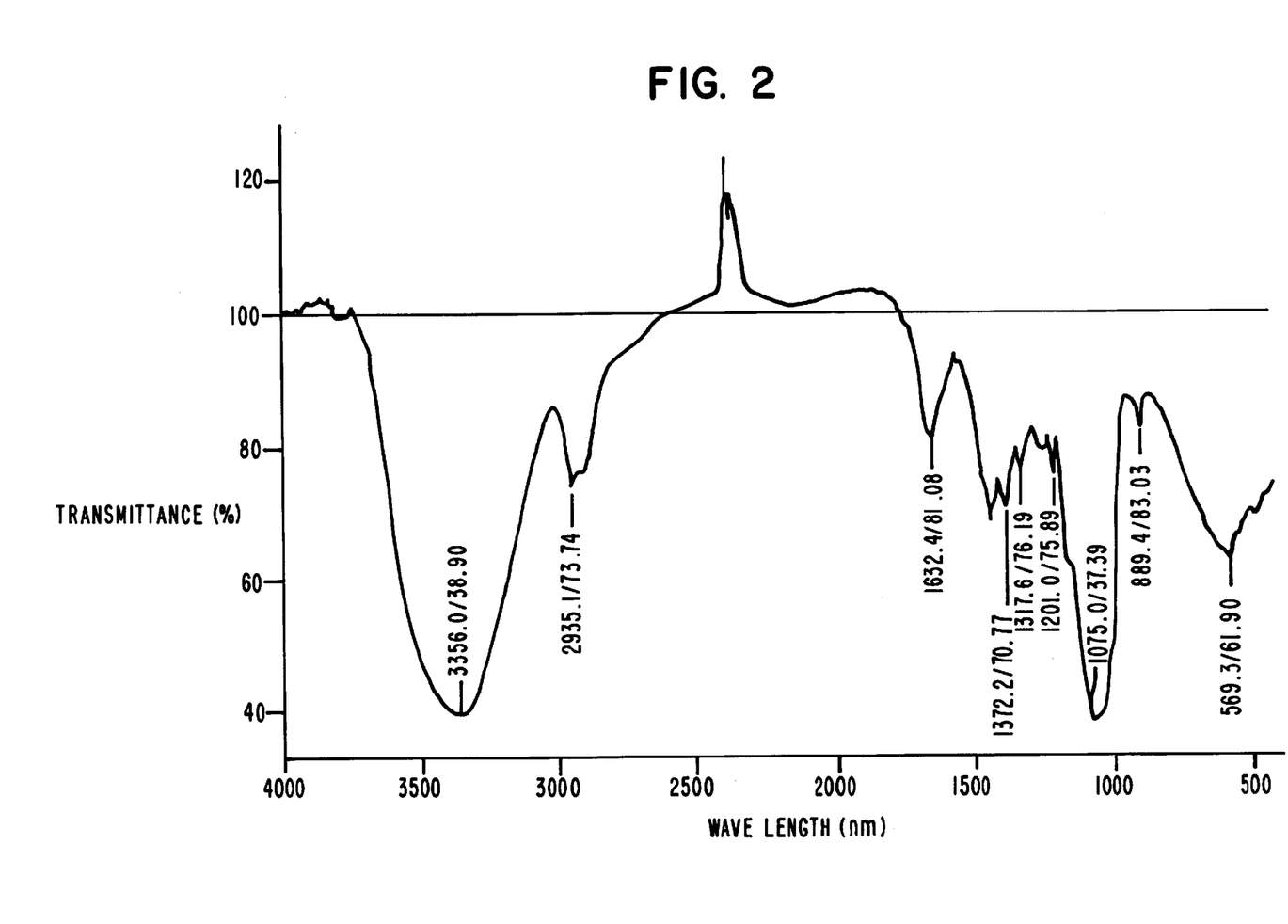
FIG. 2 is an infrared absorption spectrum of β-1,6-branched-β-1,3-glucan obtained by the present process.

The powder compound was identified by an infrared spectrophotometer(Biorad, FTS-40) and a nuclear magnetic resonance spectrophotometer(Varian Gemini-2000, 300 MHz, FT-NMR). The results were shown in FIG. 2 and FIG. 3, respectively. In FIG. 2, the β-anomer showing that the compound is primary β-glucan is confirmed at 889.4 nm and in FIG. 3, it is confirmed that this compound has an homogeneous structure having a β-1,6-D-glucose branched to every three β-1,3-D-glucose.

Figure 3:
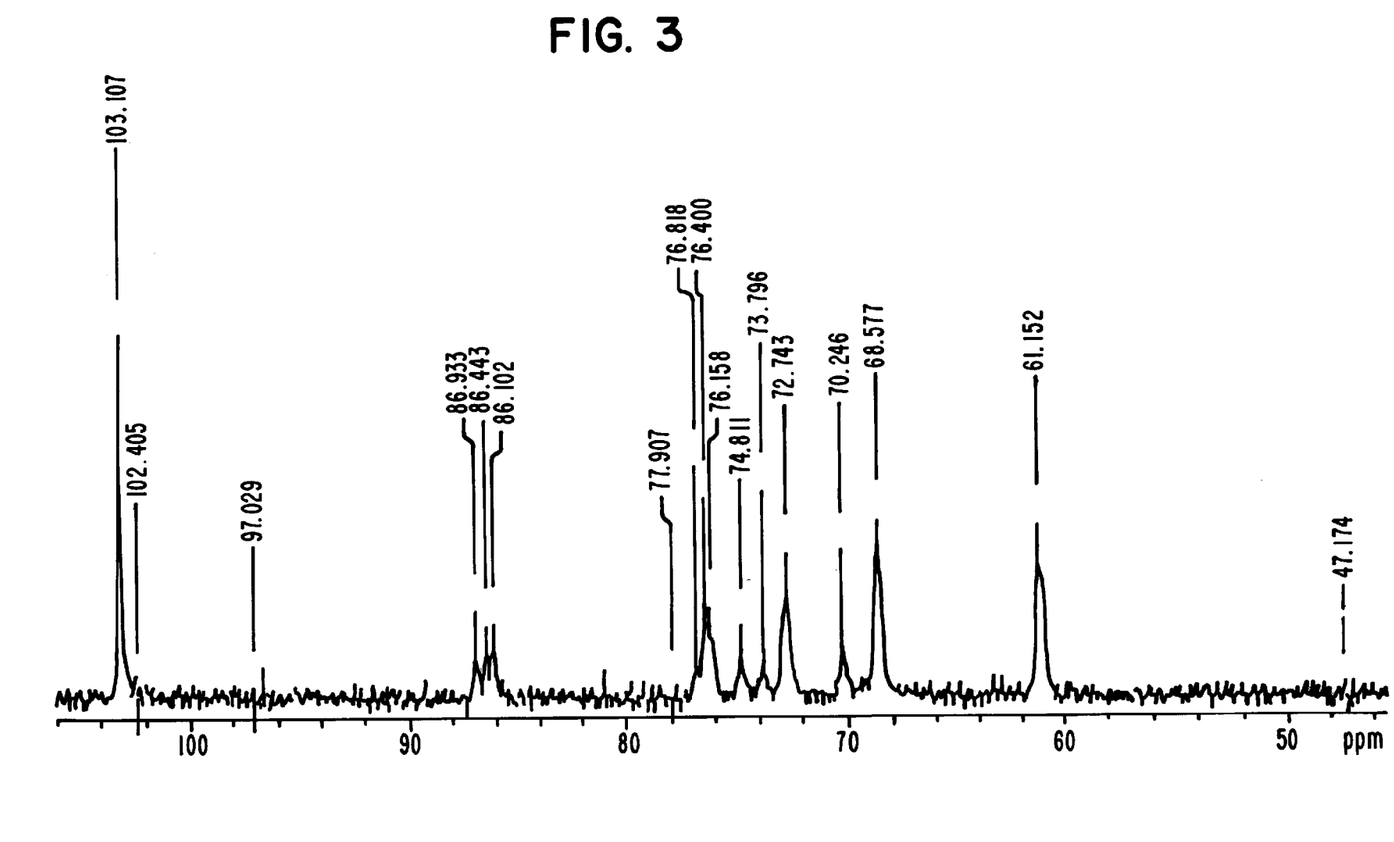
FIG. 3 is a nuclear magnetic resonance spectrum of β-1,6-branched-β-1,3-glucan obtained by the present process.

$^{13}C$ NMR(ppm): C-6(61.15), C4(68.58), C-6(70.25), C-2 (72.74), C-2(73.80), C-3(74.81), C-5(76.40), C-3(86.44), C-1(103.11)

Further, the purity of β-1,6-branched-β-1,3-glucan was measured with BGSTER A kit utilizing reaction of amoebocyte lysate of horseshoe crab and β-glucan(Wako Pure Chemical Industries, Ltd.). As a result, the purity of this compound is 99.2%.

Preparation 2

The mycelia of *Schizophyllum commune* Fr. after aseptical homogenization, were inoculated in an amount of 3% (V/V) into a liquid medium with pH of 6.5 comprising 3% by weight of glucose, 0.3% by weight of yeast extract, 0.05% of $(NH_4)_2SO_4$, 0.1% by weight of $KH_2PO_4$ and 0.05% by weight of $MgSO_4$ $7H_2O$. The liquid cultivation was performed by maintaining the medium at a temperature of 28° C., under an agitation of 200 rpm and an aeration of 1 vvm, in fermentation tank of 30 l, for 3 days. Then, to the medium was added activated charcoal powders(Jeil Chemical Co., Ltd., Korea) in an amount of 0.5%, and then the cultivation was continued for further 3 days at the same conditions. After the cultivation was completed, the concentration of the mycelia was about 3.8 g/l and the concentration of β-1,6-branched-β-1,3-glucan was about 12.3 g/l.

Next, the culture was press-filtered, and then thereto activated charcoal powders(Jeil Chemical Co., Ltd., Korea) were added in an amount of 0.5%. Then, the mixture was stirred for 30 minutes.

Next, for the purification of β-1,6-branched-β-1,3-glucan, the same procedure as described in Preparation 1 was followed.

The obtained product was identified as β-1,6-branched-β-1,3-glucan whose purity was measured 99.5%.

Preparation 3

The mycelia of *Schizophyllum commune* Fr., after aseptical homogenization, were inoculated in an amount of 3% (V/V) into a liquid medium with pH of 6.5 comprising 2% by weight of glucose, 0.4% by weight of yeast extract, 0.05% of $(NH_4)_2HPO_4$, 0.1% by weight of $KH_2PO_4$ and 0.05% by weight of $MgSO_4 \cdot 7H_2O$. The liquid cultivation was performed by maintaining the medium at a temperature of 28° C., under an agitation of 200 rpm and an aeration of 1 vvm, in fermentation tank of 30 l, for 4 days. Then, to the medium was added glucose in an amount of 0.3%, and then the cultivation was continued for further 2 days at the same conditions. After the cultivation was completed, the concentration of the mycelia was about 4.5 g/l and the concentration of β-1,6-branched-β-1,3-glucan was about 13.1 g/l.

Next, for the isolation and the purification of β-1,6-branched- β-1,3-glucan, the same procedure as described in Preparation 1 was followed.

The obtained product was identified as β-1,6-branched-β1,3-glucan whose purity was measured 99.4%.

Preparation 4

The mycelia of *Schizophyllum commune* Fr., after aseptical homogenization, were inoculated in an amount of 3% (V/V) into a liquid medium with pH of 6.5 comprising, 2% by weight of glucose, 0.4% by weight of yeast extract, 0.05% of $(NH_4)_2SO_4$, 0.1% by weight of $KH_2PO_4$ and 0.05% by weight of $MgSO_4 \cdot 7H_2O$. The liquid cultivation was performed by maintaining the medium at a temperature of 28° C., under an agitation of 200 rpm and an aeration of 1 vvm, in fermentation tank of 30 l, for 4 days. Then, to the medium was added 0.5% of activated charcoal and 3% of glucose, and then the cultivation was continued at the same conditions for further 2 days. After the cultivation was completed, the concentration of the mycelia was about 4.5 g/l 4 and the concentration of β-1,6-branched-β-1,3-glucan was about 15.1 g/l (See FIG. 4).

Next, for the isolation and the purification of β-1,6-branched-β-1,3-glucan the same procedure as described in Preparation I was followed.

The obtained product was identified as β-1,6-branched-β-1,3-glucan whose purity was measured 99.6%.

Experimental Example 1

Proliferation of Fibroblast

The human fibroblast was cultured on Dulbecco's Modified Eagle's Media(DMEM) containing 2.5% of bovine fetal serum, and then was added on 96-well microtiter plate to 5,000 cells/well.

The samples were prepared:

β-1,6-Branched-β-1,3-glucan of the Preparation 1: 1% of solution and its consecutive dilutions;

β-1,6-Branchedβ1,3-glucan of the Preparation 4: 1% of solution and its consecutive dilutions;

GluCare-S, β-glucan isolated form the yeast (Cosmoferm): 1% of solution and its consecutive dilutions; and The filtrate before the precipitation with ethyl alcohol in the Preparation 1: 100% and its 1/10 consecutive dilutions.

After the addition of each sample into each well, the 96-well plate was maintained at 37° C. for 4 days. After the cultivation was completed, 0.2% of 3-[4,5-dimethylthiazol-2-yl]-2,5diphenyltertazolium bromide(MTT) was added to 50 μl/well.

Again, the plate was maintained at 37° C. for 4 days to give formazan. After dissolving the formazan in dimethyl sulfoxide, the absorbance at 570 nm was measured with microplate reader. The proliferation of fibroblast were evaluated by comparing the absorbance with that of the control group with no sample treated. The results are shown in Table 1.

TABLE 1

| Concentration of the samples (%) | Preparation 1 | Preparation 4 | Glu-Care-S | Concentration (%) | The filtrate of the Preparation 1 |
|---|---|---|---|---|---|
| $4 \times 10^{-7}$ | 5 | 5 | 0 | $1 \times 10^{-2}$ | 5 |
| $4 \times 10^{-6}$ | 6 | 5 | 0 | $1 \times 10^{-1}$ | 10 |
| $4 \times 10^{-5}$ | 5 | 7 | 1 | $1 \times 10^{0}$ | 15 |
| $4 \times 10^{-4}$ | 6 | 7 | 3 | $1 \times 10^{1}$ | 17 |
| $8 \times 10^{-4}$ | 15 | 16 | 5 | $1 \times 10^{2}$ | 14 |
| $4 \times 10^{-3}$ | 34 | 28 | 7 | | |
| $4 \times 10^{-2}$ | 40 | 35 | 7 | | |
| $4 \times 10^{-1}$ | 38 | 34 | 5 | | |

As shown in Table 1, the treatment with GluCare-S leads to maximum 7% increase, in the proliferation of the fibroblast. While, the treatment β-1,6-branched-β-1,3-glucan isolated from *Schizophyllum commune* Fr. leads to maximum 40% increase. However, the filtrate before purification of β-1,6-branched-β-1,3-glucan(extract of *Schizophyllum commune* Fr.) is less effective in proliferating fibroblast.

Experimental Example 2

Proliferation of Keratinocyte

The same procedure as described in Experimental Example 1 was followed by Keratinocyte, instead of fibroblast, to evaluated the proliferation of keratinocyte. The results are shown in Table 2.

TABLE 2

| Concentration of the samples (%) | Preparation 1 | Preparation 4 | Glu-Care-S | Concentration (%) | The filtrate of The Preparation 1 |
|---|---|---|---|---|---|
| $4 \times 10^{-7}$ | 5 | 3 | 0 | $1 \times 10^{-2}$ | 5 |
| $4 \times 10^{-6}$ | 5 | 3 | 0 | $1 \times 10^{-1}$ | 10 |
| $4 \times 10^{-5}$ | 7 | 5 | 1 | $1 \times 10^{0}$ | 13 |
| $4 \times 10^{-4}$ | 11 | 10 | 3 | $1 \times 10^{1}$ | 8 |
| $8 \times 10^{-4}$ | 19 | 15 | 10 | $1 \times 10^{2}$ | 6 |
| $4 \times 10^{-3}$ | 20 | 19 | 12 | | |
| $4 \times 10^{-2}$ | 19 | 16 | 11 | | |
| $4 \times 10^{-1}$ | 18 | 15 | 8 | | |

As shown in Table 1, the treatment with GluCare-S leads to maximum 12% increase in the proliferation of the keratinocyte. While, the treatment β-1,6-branched-β-1,3-glucan isolated from *Schizophyllum commune* Fr. leads to maximum 20% increase. However, the filtrate before purification of β-1,6-branched-β-1,3-glucan(extract of *Schizophyllum commune* Fr.) is less effective in proliferating keratinocyte.

Experimental Example 3

Biosynthesis of Collagen of Fibroblast

The fibroblast was cultured on 24-well microtiter plate containing the same medium and treated with the same samples as those of Experimental Ex. 1, for 3 days. After the cultivation was completed, 0.5 µl of DMEM and 10 µCi of L[2,3,4,5-³H]-proline were added into each well. 24 hours later, the median and the cells contained in each well were recovered and washed with 5% of trichloroacetic acid, and then divided into two test tubes. To one of two test tubes was added 1 unit/µl of type I collagenase, and then the test tube was maintained at 37° C. for 90 minutes. The other test tube was incubated at 4° C. Then, 0.05 µl of 50% of trichloroacetic acid was added to each of two test tubes, which was maintained at 4° C. for 20 minutes. The resulting solution was centrifuigated at 12,000 rpm for 10 minutes and then, the decay per minute (dpm) of the supernatant and of the precipitate was measured with Liquid Scintillation Counter. Relative Collagen Biosynthesis(RCB) is calculated by the following equation.

RCB=[collagen *dpm*/{(total collagen−collagen *dpm*)×5.4+collagen *dpm*}]×100

The results are shown in Table 3.

TABLE 3

| Concentration of the samples (%) | Preparation 1 | Preparation 4 | Glu-Care-S | Concentration (%) | The filtrate of the Preparation 1 |
|---|---|---|---|---|---|
| $4 \times 10^{-6}$ | 5 | 0 | 0 | 0 | 0 |
| $4 \times 10^{-5}$ | 5 | 5 | 1 | $1 \times 10^{-2}$ | 0 |
| $4 \times 10^{-4}$ | 11 | 8 | 3 | $1 \times 10^{-1}$ | 5 |
| $4 \times 10^{-3}$ | 22 | 21 | 5 | $1 \times 10^{0}$ | 12 |
| $4 \times 10^{-2}$ | 32 | 30 | 5 | $1 \times 10^{1}$ | 10 |
| $4 \times 10^{-1}$ | 24 | 23 | 3 | $1 \times 10^{2}$ | 6 |

As shown in Table 3, the treatment with GluCare-S leads to maximum 5% increase in the biosynthesis of collagen of the fibroblast, while the treatment with β-1,6-branched-β-1,3-glucan isolated from *Schizophyllum commune* Fr. leads to maximum 32% increase. However, the filtrate before purification of β-1,6-branched-β-1,3-glucan(extract of *Schizophyllum commune* Fr.) is less effective in promoting biosynthesis of collagen.

Experimental Example 4

Cure Effect of the Skin Demage Caused by Excessive Sun Exposure

The skin-color was measured with Chromameter CM2002 before the irradiation of UV-ray MED of the upper arm of volunteer was measured with Solar simulator and then thereto was irradiated U.V-ray to make 1.5 MED inducing erythema. At 6, 8, 10, 24 hours after the irradiation, to the subject was applied 20 µl of the same sample (1of β1,6-branched-β-1,3-glucan and 100% of the filtrate) in the Experimental Example 1. Before and after the treatment with the samples, the skin-color was measured with Chromameter CM2002. The relative value, when the skin-color before the irradiation of UV is converted to "100", is calculated as "erythema index" which was verified the statistical significance by Anova test($p<0.05$). From this index, the cure evaluated. The results are shown in Table 4.

TABLE 4

| | (Unit; erythema index) | | | |
|---|---|---|---|---|
| Hour | Control (D.W.) | Preparation 1 | GluCare-S | The filtrate of the Preparation 1 |
| 0 | 100.00 | 100.00 | 100.00 | 100.00 |
| 16 | 197.85 | 163.60 | 193.51 | 180.65 |
| 24 | 193.58 | 155.01 | 189.32 | 178.28 |
| 48 | 174.98 | 135.87 | 165.25 | 160.56 |

As shown Table 4, the treatment with GluCare-S leads to maximum 5.56% cure efficacy for the demaged skin, while the treatment with β-1,6-branched-β-1,3-glucan isolated from *Schizophyllum commune* Fr. leads to maximum 22.35% cure efficacy. However the filtrate before purification of β-1,6-branched-β-1,3-glucan(extract of *Schizophyllum commune* Fr.) is less effective in curing the damaged skin.

Example 5

Whitening Effect

To upper arms of ten healthy male volunteers were applied opaque tapes having six holes of 1.5 cm diameter and were irradiated with U.V-ray with TL20W/09UV lamp (Philips) and TL20W/12UV lamp(Philips) at a level of 200 mJ/cm². Two weeks later, to the subject was applied 0.1% of β-1,6branched-β-1,3-glucan of the Preparation 4, 0.1% of GluCare-S and 25% dilution of the filtrate before the precipitation with ethyl alcohol in the preparation 1, every two times a day for 2 months. Before and the treatment with the samples, the skin-color was measured with Chromameter CM2002, at a constant interval. The difference of the whiteness($\Delta L$) compared with the whiteness of the skin before the application of the samples was calculated and the results are shown

TABLE 5

| Application period of the sample (days) | (Unit: ΔL) | | | |
|---|---|---|---|---|
| | Control | Preparation 4 | GluCare-S | The filtrate of the Preparation 1 |
| 0 | 0 | 0 | 0 | 0 |
| 10 | 0.25 | 0.95 | 0.31 | 0.61 |
| 20 | 0.50 | 2.15 | 0.52 | 1.50 |
| 30 | 1.00 | 2.65 | 1.35 | 2.00 |
| 40 | 1.74 | 3.52 | 2.12 | 2.54 |
| 50 | 2.37 | 4.2 | 2.75 | 2.90 |
| 60 | 2.93 | 4.71 | 3.20 | 3.35 |

As shown in Table 5, β-1,6-branched-β-1,3-glucan isolated from *Schizopyllum commune* Fr. is the most effective in improving whiteness of the skin.

Experimental Example 6

Improvement of Skin Wrinkling

In order to evaluate the ability to improve the skin wrinkling for the composition containing β-1,6-branched-β-1,3-glucan, the following experiment was, carried out. Ten(10) volunteers aging 35~45 years used nutrient creams of Example 1 and comparative Example 1

| | (unit: % by weight) | |
|---|---|---|
| Material | Example 1 | Comparative Ex. 1 |
| β-1,6-Branched-β-1,3-glucan of Preparation Ex. 1 | 0.1 | — |
| Bees wax | 3.0 | 3.0 |
| Polysorbate 60 | 1.5 | 1.5 |
| PEG-60 hardened castor oil | 2.0 | 2.0 |
| Sorbitan sesquioleate | 0.5 | 0.5 |
| Liquid paraffin | 10.0 | 10.0 |
| Squalane | 5.0 | 5.0 |
| Caprylic/capric triglyceride | 5.0 | 5.0 |
| Glycerine | 5.0 | 5.0 |
| Butyleneglycol | 3.0 | 3.0 |
| Propyleneglycol | 3.0 | 3.0 |
| Triethanolamine | 0.2 | 0.2 |
| Preservative | q.s. | q.s. |
| Pigment | q.s. | q.s. |
| Perfume | q.s. | q.s. |
| Distilled water | to 100 | to 100 |

To the right face was applied the nutrient creams of Example 1 and to left face was applied the nutrient creams of Comparative Example 1, for 3 months. The improvement of the skin-wrinkles was evaluated by comparing the wrinkles of eye-tail before and after the use of creams. The wrinkles of eye-tail were taken with replica and measured with Visiometer system(C+K) in constant temperature and humidity room set to a temperature of 24° C. and relatively humidity of 40%. The improvement of skin-wrinkles were calculated by the following equation:

Improvement of wrinkles $(\Delta\%) = \{(Tdi - Tdo)/Tdo\} \times 100$ (Wherein,

Tdi is skin-wrinkles value measured after the use of the creams

Tdo is skin-wrinkles value measured before the use of the creams)

As a result, the improvement in the left face was 3.1±2.2%, while the improvement in the right face was 15±4.1%.

The compositions for external application containing β-1, 6-branched-β-1,3-glucan will be illustrated in more detail by way of the following Formulations 1~9. However, these formulations are provided for only illustration purpose and should not be constructed as limiting the scope of the invention which is properly delineated in the accompanying claims.

(Formulation 1) Skin lotion

| Materials | % by weight |
|---|---|
| β-1,6-Branched-β-1,3-glucan of Preparation Ex. 1 | 0.1 |
| Glycerine | 3.0 |
| Butyleneglycol | 2.0 |
| Propyleneglycol | 2.0 |
| Carboxy vinyl polymer | 0.1 |
| PEG-12 nonylphenyl ether | 0.2 |
| Polysorbate 80 | 0.4 |
| Ethanol | 10.0 |
| Triethanolamine | 0.1 |
| Preservative | q.s |
| Pigment | q.s |
| Perfume | q.s |
| Distilled water | to 100 |

(Formulation 2) Milk lotion

| Material | % by weight |
|---|---|
| β-1,6-Branched-β-1,3-glucan of Preparation Ex. 4 | 0.1 |
| Squalane | 5.0 |
| Bees wax | 4.0 |
| Polysorbate 60 | 1.5 |
| Sorbitan sesquioleate | 1.5 |
| Liquid paraffin | 0.5 |
| Caprylic/capric triglyceride | 5.0 |
| Glycerine | 3.0 |
| Butyleneglycol | 3.0 |
| Propyleneglycol | 3.0 |
| Carboxy vinyl polymer | 0.1 |
| Triethanolamine | 0.2 |
| Preservative | q.s. |
| Pigment | q.s. |
| Perfume | q.s. |
| Distilled water | to 100 |

(Formulation 3) Nutrient creams

| Material | % by weight |
|---|---|
| β-1,6-Branched-β-1,3-glucan of Preparation Ex. 2 | 0.1 |
| Bees wax | 10.0 |
| Polysorbate 60 | 1.5 |
| PEG-60 hardened castor oil | 2.0 |
| Sorbitan sesquioleate | 0.5 |
| Liquid parrafin | 10.0 |
| Squalane | 5.0 |
| Caprylic/capric triglyceride | 5.0 |
| Glycerine | 5.0 |
| Butyleneglycol | 3.0 |
| Propyleneglycol | 3.0 |
| Triethanolamine | 0.2 |
| Preservative | q.s. |
| Pigment | q.s. |
| Perfume | q.s. |
| Distilled water | to 100 |

(Formulation 4) Masage creams

| Material | % by weight |
|---|---|
| β-,1,6-Branched-β-1,3-glucan of Preparation Ex. 3 | 0.1 |
| Bees wax | 10.0 |
| Polysorbate 60 | 1.5 |
| PEG-60 hardened castor oil | 2.0 |
| Sorbitan sesquioleate | 0.8 |
| Liquid paraffin | 40.0 |
| Squalane | 5.0 |
| Caprylic/capric triglyceride | 4.0 |
| Glycerine | 5.0 |
| Butyleneglycol | 3.0 |
| Propyleneglycol | 3.0 |
| Triethanolamine | 0.2 |
| Preservative | q.s. |
| Pigment | q.s. |
| Perfume | q.s. |
| Distilled water | to 100 |

(Formulation 5) Pack

| Material | % by weight |
|---|---|
| β-1,6-Branched-β-1,3-glucan of Preparation Ex. 1 | 0.1 |
| Polyvinyl alcohol | 13.0 |
| Sodium carboxymethyl cellulose | 0.2 |
| Glycerine | 5.0 |
| Alantoin | 0.1 |
| Ethanol | 6.0 |
| PEG-12 nonylphenyl ether | 0.3 |
| Polysorbate 60 | 0.3 |
| Preservative | q.s. |
| Pigment | q.s. |
| Perfume | q.s. |
| Distilled water | to 100 |

(Formulation 6) Gel

| Material | % by weight |
|---|---|
| β-1,6-Branched-β-1,3-glucan of Preparation Ex. 4 | 0.1 |
| Ethylenediamine sodium acetate | 0.05 |
| Glycerine | 5.0 |
| Carboxyvinyl polymer | 0.3 |
| Ethanol | 5.0 |
| PEG-60 hardened caster oil | 0.5 |
| Triethanolamine | 0.3 |
| Preservative | q.s. |
| Pigment | q.s. |
| Perfume | q.s. |
| Distilled water | to 100 |

(Formulation 7) Ointment

| Material | % by weight |
|---|---|
| β-1,6-Branched-β-1,3-glucan of Preparation Ex. 4 | 0.1 |
| Bees wax | 10.0 |
| Polysorbate 60 | 5.0 |
| PEG-60 hardened caster oil | 2.0 |
| Sorbitan sesquioleate | 0.5 |
| Vaseline | 5.0 |
| Liquid parraffin | 10.0 |
| Squalane | 5.0 |

(Formulation 7) Ointment -continued

| Material | % by weight |
|---|---|
| Sheabutter | 3.0 |
| Caprylic/capric triglyceride | 5.0 |
| Glycerine | 10.0 |
| Propyleneglycol | 10.2 |
| Triethanolamine | 0.2 |
| Preservative | q.s. |
| Pigment | q.s. |
| Perfume | q.s. |
| Distilled water | to 100 |

(Formulation 8) Gel type ointment

| Material | % by weight |
|---|---|
| β-1,6-Branched-β-1,3-glucan of Preparation Ex. 4 | 3.0 |
| Polyacrylic acid (Carbopol 940) | 1.5 |
| Isopropanol | 5.0 |
| Hexyleneglycol | 25.0 |
| Triethanolamine | 1.7 |
| Deionized water | to 100 |

(Formulation 9) Patch

| Materials | % by weight |
|---|---|
| β-1,6-Branched-β-1,3-glucan of Preparation Ex. 4 | 0.1 |
| Hexyleneglycol | 20.0 |
| Diethylamine | 0.7 |
| Polyacrylic acid (Carbopol 934P) | 1.0 |
| Sodium sulfite | 0.1 |
| Polyoxyethylene lauryl ether (E.O = 9) | 1.0 |
| Polyhydroxyethylene cetyl stearyl ether (Cetomacrogol 1000) | 1.0 |
| Viscous Paraffin oil | 2.5 |
| Caprylic ester/capric ester (Cetiol LC) | 2.5 |
| Polyethyleneglycol 400 | 3.0 |
| Deionized water | to 100 |

What is claimed is:

1. A method of promoting proliferation of skin cells of an individual, comprising topically administering to the individual a composition in an amount effective to cause proliferation of skin cells, wherein the composition comprises a purified β-1,6-branched-β-1,3-glucan from *Schizophyllum commune*.

2. A method of promoting collagen biosynthesis in the skin of an individual, comprising topically administering to the individual a composition in an amount effective to promote collagen biosynthesis in skin cells, wherein the composition comprises a purified β-1,6-branched-β1,3-glucan from *Schizophyllum commune*.

3. A method of promoting skin whitening, comprising topically administering to an individual a composition in an amount effective to whiten skin, wherein the composition comprises a purified β-1,6-branched-β-1,3-glucan from *Schizophyllum commune*.

4. A method of reducing skin wrinkling, comprising topically administering to an individual with skin wrinkles a composition in an amount effective to reduce wrinkles, wherein the composition comprises a purified β-1,6-branched-β1,3-glucan from *Schizophyllum commune*.

* * * * *